United States Patent [19]

Van Scott et al.

[11] 4,361,571
[45] Nov. 30, 1982

[54] 3-CARBAMOYL-6-AMINOPYRIDINIUM AND ANALOGUES, AND THEIR USE IN TREATING SKIN DISORDERS

[76] Inventors: Eugene J. Van Scott, 1138 Sewell La., Rydal, Pa. 19046; Ruey J. Yu, 4 Lindenwold Ave., Ambler, Pa. 19002

[21] Appl. No.: 226,841

[22] Filed: Jan. 21, 1981

[51] Int. Cl.$^3$ .................. C07D 211/98; A61K 31/455
[52] U.S. Cl. .................................... 424/266; 546/309; 546/310; 536/23; 536/24; 536/26; 536/27; 536/28; 536/29; 424/180
[58] Field of Search ................ 424/266; 546/309, 310

[56] References Cited

U.S. PATENT DOCUMENTS

| | | | |
|---|---|---|---|
| 2,199,839 | 5/1940 | Renshaw et al. | 546/310 |
| 4,067,975 | 1/1978 | Yu et al. | 424/266 |
| 4,141,977 | 2/1979 | Yu et al. | 546/310 |

*Primary Examiner*—Jane T. Fan
*Attorney, Agent, or Firm*—Le Blanc, Nolan, Shur & Nies

[57] ABSTRACT

Systemic as well as topical treatment to alleviate the symptoms of skin disorders characterized by inflammation or disturbed keratinization comprising as the principal active ingredient, one or more 3-carbamoyl-6-aminopyridinium compounds, is disclosed. In the topical treatment the therapeutic composition may include one or more of the above active ingredients present in a total amount of from 0.01 to 5 percent by weight of the total composition. In the systemic treatment oral administration or parenteral injection in a total dosage of from 1 mg/kg to 50 mg/kg has been found to achieve a substantial improvement to complete remissions of the skin lesions, and to ameliorate the symptoms of arthritis that may be associated therewith.

33 Claims, No Drawings

3-CARBAMOYL-6-AMINOPYRIDINIUM AND ANALOGUES, AND THEIR USE IN TREATING SKIN DISORDERS

This invention relates to systemic as well as topical treatment of the symptoms of psoriasis and other skin disorders, and specifically to 3-carbamoyl-6-aminopyridinium compounds and analogues thereof which have been found to be effective against these conditions.

In our prior Patent Application Ser. No. 009,589, filed Feb. 5, 1979, it was disclosed that 6-substituted nicotinamides, 1,6-disubstituted 1,6-dihydronicotinamides and 1 substituted-6-amino-1,2-dihydronicotinamides and analogues thereof were effective in treating the symptoms of psoriasis by topical application. In our prior Patent Application Ser. No. 715,131, filed Aug. 17, 1976, now U.S. Pat. No. 4,141,977, we described and claimed our discovery that certain 6-substituted nicotinamides and 2-substituted pyrazinamides were effective in topical treatment of psoriasis. In our parent Patent Application Ser. No. 601,411, now U.S. Pat. No. 4,067,975, we described our discovery that 6-aminonicotinamide and thionicotinamide in medicinal compositions are effective in the treatment of psoriasis. The disclosure of these prior cases are hereby incorporated by reference.

It has now been discovered that a unique group of pyridinium compounds is also effective for topical and additionally for systemic treatment of various skin disorders including those characterized by inflammation of disturbed keratinization.

In accordance with the present invention the pyridinium compounds are 3-carbamoyl-6-aminopyridinium compounds and analogues. As will be subsequently described these compounds have been found to be useful for systemic as well as topical treatment to alleviate the symptoms of skin disorders. The compounds may be grouped in the following three classes:

The first class of compounds is 6-aminonicotinamide pyridinium derivatives having the following chemical structure:

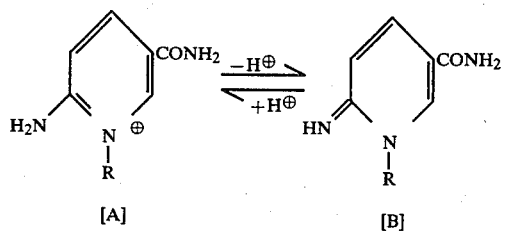

wherein R=an alkyl or aryl radical having 1-to-19 carbon atoms with or without substituent elements such as O, N, P and S atoms.

The compounds may be present as a charged form [A] or uncharged form [B]. When charged, form [A], the pyridinium compound is a cation i.e. an ion having a positive charge. It will form a salt with anions i.e. ions having a negative charge. Common anions used to form salts include iodide, bromide, chloride, sulfate, nitrate, phosphate, carbonate and hydroxide ions. When the pyridinium compound has an anion forming group such as phosphoric, carboxylic or sulfonic acid attached to the substituent at position 1 (ring nitrogen atom) the salt thus formed is called an inner salt, i.e., intramolecular salt.

Representative 6-aminonicotinamide pyridinium compounds which are useful for systemic as well as topical treatment of skin disorders are listed below; the anions may be replaced by any other common anions such as those listed above.

1. 1-Methyl-3-carbamoyl-6-aminopyridinium iodide.
2. 1-Phenyl-3-carbamoyl-6-aminopyridinium iodide.
3. 1-Carbamoylmethyl-3-carbamoyl-6-aminopyridinium iodide.
4. 1-Carboxymethyl-3-carbamoyl-6-aminopyridinium iodide.
5. 1-Cyanomethyl-3-carbamoyl-6-aminopyridinium iodide.
6. 1-Benzyl-3-carbamoyl-6-aminopyridinium iodide.
7. 1-Ribosyl-3-carbamoyl-6-aminopyridinium chloride also called 6-Aminonicotinamide nucleoside.
8. 1-Phosphonoribosyl-3-carbamoyl-6-aminopyridinium hydroxide inner salts also called 6-Aminonicotinamide mononucleotide.
9. 1-Diphosphonoribosyl-3-carbamoyl-6-aminopyridinium hydroxide inner salt are called 6-Aminonicotinamide dinucleotide.
10. 1-Ribosylphosphonoribosyl-3-carbamoyl-6-aminopyridinium hydroxide inner salt.
11. 1-Ribosyldiphosphonoribosyl-3-carbamoyl-6-aminopyridinium hydroxide inner salt.
12. 1-Adenine-ribosyl-diphosphono-ribosyl-3-carbamoyl-6-aminopyridinium hydroxide inner salt also called 6-Aminonicotinamide adenine dinucleotide or 6-Amino NAD.
13. The ribose in the above mentioned substituent at position 1 may be replaced by other carbohydrates such as threose, erythrose, arabinose, xylose, Lyxose, allose, altrose, glucose, mannose, gulose, idose, galactose or talose.
14. The adenine in the above mentioned substituent at position 1 may be replaced by another purine or pyrimidine base such as guanine, hypoxanthine, thymine, uracil or cytosine.
15. The hydroxyl group in the above mentioned substituent at position 1 may be in ester form such as acetate, benzoate, phosphate, sulfonate or sulfate.

The second class of compounds is 6-aminonicotinic acid pyridinium derivatives and their salts, as shown by the following chemical structure:

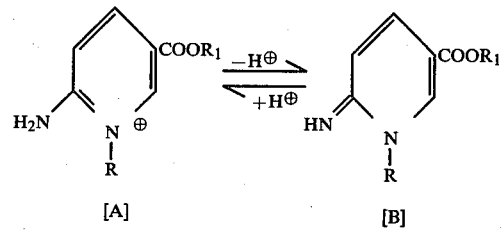

wherein
$R_1$=H or an inorganic or organic cation
R=an alkyl or aryl radical of 1-to-19 carbon atoms with or without substituent elements such as O, N, P and S atoms.

The compounds may be present as a charged form [A] or uncharged form [B]. When charged, form [A], the pyridinium compound may form either an intramolecular or intermolecular salt as described above in connection with the first class of compounds.

Representative 6-aminonicotinic acid pyridinium compounds and their salts which are useful for systemic as well as topical treatment of skin disorders are the same as those listed in the first class of compounds except that the 3-carbamoyl group is replaced by a 3-carboxyl group, or its inorganic or organic salt.

The third class of compounds is 6-aminonicotinate pyridinium derivatives, as shown by the following chemical structure:

$$\underset{\underset{R}{\overset{|}{N}}}{\underset{H_2N}{\bigcirc}}\overset{COOR_1}{\underset{\oplus}{\phantom{X}}} \underset{+H^{\oplus}}{\overset{-H^{\oplus}}{\rightleftharpoons}} \underset{\underset{R}{\overset{|}{N}}}{\underset{HN}{\bigcirc}}\overset{COOR_1}{\phantom{X}}$$

[A]  [B]

wherein $R_1$ = an alkyl or aryl radical of 1-to-9 carbon atoms

R = an alkyl or aryl radical of 1-to-19 carbon atoms with or without other substituent elements such as O, N, P and S atoms.

The compounds may be present as a charged form [A] or uncharged form [B]. When charged, form [A], the pyridinium compounds may form either an intramolecular or an intermolecular salt as described above in connection with the first class of compounds.

Representative 6-aminonicotinate pyridinium which are useful for systemic as well as topical treatment of skin disorders are the same as those listed in the first class of compounds except that the 3-carbamoyl group is replaced by a 3-carboxyl ester group.

In addition to the above three classes of 6-aminonicotinamide pyridinium compounds the thiol analogue may also be included. In this instance the 3-carbamoyl, 3-carboxyl or 3-carboxyl ester group is replaced by the 3-thiocarbamoyl, B 3-thiocarboxyl or 3-thio-carboxyl ester group.

It has been established through tests on humans having psoriasis, dry skin, Sèzary's syndrome, pityriasis rubra pilaris, Darier's disease and other inflammatory disorders and disorders of keratinization that systemic or topical administration of 6-aminonicotinamide pyridinium compounds or analogues of this invention, in a dosage or concentration of from 1 mg/kg to 50 mg/kg or from 0.01 to 5 percent, respectively, is therapeutically effective, when administered on a regular basis, to cause, within about one to four weeks, a substantial improvement with return of the affected areas to a normal state.

PREPARATION OF THERAPEUTIC COMPOSITIONS

The 6-Aminonicotinamide pyridinium compounds or analogues of this invention may be formulated either for topical application or for systemic administration. In the topical composition 6-aminonicotinamide pyridinium compounds or analogues are formulated in lotion, cream or ointment form in a concentration of from about 0.01 to 5 percent, and preferably, from 0.05 to 2 percent by weight of the total composition.

For systemic administration the 6-aminonicotinamide pyridinium compounds or analogues of this invention may be formulated for oral use or for parenteral injections. In the oral preparation the 6-aminonicotinamide pyridinium compounds or analogues may be formulated in gelatin capsules or tablets with or without mixing with gelatin powder. Each capsule may contain from 20 to 250 mg of the active ingredients. For parenteral injections 6-aminonicotinamide pyridinium compositions are prepared under sterilized conditions usually in 1 to 5 percent solutions or suspensions.

Accordingly, it is an object of this invention to provide new compounds which are 6-aminonicotinamide pyridinium derivatives or analogues, useful in treating the symptoms of skin disorders by systemic or topical administration.

It is another object of this invention to provide new compounds which are 6-aminonicotinic acid pyridinium derivatives, analogues, or salts thereof which are useful in treating the symptoms of skin diseases by systemic or topical administration.

It is still another object of this invention to provide new compounds which are 6-aminonicotinate pyridinium derivatives or analogues which are useful in treating the symptoms of skin conditions by systemic or topical administration.

These and other objects will become readily apparent with reference to the following description:

The following are illustrative examples of methods of syntheses, formulations and compositions according to this invention. Although the Examples utilize only selected formulations of this invention, it should be understood that the following examples are illustrative and not limited. Therefore, any of the aforementioned 3-carbamoyl-6-aminopyridinium and analogues may be substituted according to the teachings of this invention in the following examples.

EXAMPLE I

Synthesis of 1-Methyl-3-carbamoyl-6-aminopyridinium iodide

The following procedure may be adapted to syntheses of many 6-aminonicotinamide pyridiniums and analogues.

6-Aminonicotinamide 70 gm (0.5 mole) is mixed with 250 ml of dimethylsulfoxide and the mixture is heated to 50° C. until a clear solution is obtained. Iodomethane 45 ml (0.75 mole) is added slowly to the solution and the mixture is heated to 80°–90° C. for 30 minutes. After cooling the mixture is mixed with 700 ml of chloroform. Light yellowish crystals thus formed are isolated by filtration and are washed with methanol. Yield is 130 gm.

1-Methyl-3-carbamoyl-6-aminopyridinium iodide thus synthesized is practically pure as shown by infrared spectroscopy, high performance liquid chromatography and thin-layer chromatography with a mobility of 0.70 on a solvent system of benzene:methanol 1:1.

EXAMPLE 2

1-Methyl-3-carbamoyl-6-aminopyridinium iodide 1% cream may be prepared as follows:

1-Methyl-3-carbamoyl-6-aminopyridinium iodide as synthesized in Example 1 is ball-milled to a fine powder form. The powdered pyridinium iodide 1 gm is mixed with 99 gm of hydrophilic ointment USP. The mixing is continued until a uniform consistency is obtained.

EXAMPLE 3

1-Methyl-3-carbamoyl-6-aminopyridinium iodide 2% ointment may be prepared as follows:

1-Methyl-3-carbamoyl-6-aminopyridinium iodide powder 2 gm is mixed with 58 gm of petrolatum and 40 gm of mineral oil. The mixing is continued until a uniform consistency is obtained.

EXAMPLE 4

1-Methyl-3-carbamoyl-6-aminopyridinium iodide 1% water-in-oil cream may be prepared as follows:

| Part A: | Sorbitan sesquioleate | 10 gm |
| --- | --- | --- |
| | Petrolatum | 15 gm |
| | Mineral Oil | 15 gm |
| | Beeswax | 15 gm |
| | Isopropylmyristate | 10 gm |
| Part B: | Water | 23 ml |
| | Propylene glycol | 5 ml |
| | Glycerol | 3 ml |
| | Sorbitol | 3 gm |
| | Magnesium hydroxide | 0.1 gm |

Heat Part A and Part B to 80° C. Add Part B slowly to Part A with agitation. Continue agitation until the mixture is congealed. Add 1-methyl-3-carbamoyl-6-aminopyridinium iodide powder 1 gm to the congealed mixture. Continue agitation until a uniform consistency is obtained.

EXAMPLE 5

1-Methyl-3-carbamoyl-6-aminopyridinium hydroxide 1% cream may be prepared as follows:

1-Methyl-3-carbamoyl-6-aminopyridinium iodide 5.6 gm (0.02 mole) is dissolved in 400 ml of water. Wet silver oxide 5.4 gm (0.03 mole) is added to the solution with agitation. Silver iodide is formed instantly. After one hour of agitation the mixture is filtered to remove silver iodide and excess silver oxide. The filtrate is lyophilized to remove water. 1-Methyl-3-carbamoyl-6-aminopyridinium hydroxide thus prepared 1 gm is mixed with 99 gm of hydrophilic ointment USP. The mixing is continued until a uniform consistency is obtained.

EXAMPLE 6

1-Methyl-3-carbamoyl-6-aminopyridinium chloride 2% cream may be prepared as follows:

1-Methyl-3-carbamoyl-6-aminopyridinium iodide 5.6 gm (0.02 mole) is dissolved in 400 ml of water. Wet silver oxide 5.4 gm (0.03 mole) is added to the solution with agitation. After one hour of agitation the mixture is filtered to remove silver iodide and excess silver oxide. Hydrochloric acid 2 N solution is added to the filtrate until pH4.0. The mixture is filtered again and is lyophilized. 1-Methyl-3-carbamoyl-6-aminopyridinium chloride thus prepared 2 gm is mixed with 98 gm of hydrophilic ointment USP. The mixing is continued until a uniform consistency is obtained.

EXAMPLE 7

Synthesis of 1-carbamoylmethyl-3-carbamoyl-6-aminopyridinium iodide

6-Aminonicotinamide 14 gm (0.1 mole) and iodoacetamide 37 gm (0.2 mole) are added to 100 ml dimethylsulfoxide, and the mixture is heated to 60° C. for five hours. During this reaction period the mixture changes in color from slight yellowish to dark reddish solution. Chloroform 800 ml is added to the reaction mixture and the precipitate thus formed is separated by filtration. The precipitate is washed three times with 200 ml ethanol and are dried at 40° C. in a vacuum.

1-carbamoylmethyl-3-carbamoyl-6-aminopyridinium iodide 29 gm thus synthesized is practically pure as shown by infrared spectroscopy, high performance liquid chromatography and thin-layer chromatography with a mobility of 0.34 on a solvent system of benzene:methanol 1:1.

EXAMPLE 8

1-Carbamoylmethyl-3-carbamoyl-6-aminopyridinium iodide 0.2% cream may be prepared as follows:

1-Carbamoylmethyl-3-carbamoyl-6-aminopyridinium iodide 0.2 g is mixed with 99.8 gm of hydrophilic ointment USP. The mixing is continued until a uniform light brownish consistency is obtained.

EXAMPLE 9

For oral administration gelatin capsules containing 1-methyl-3-carbamoyl-6-aminopyridinium iodide in different doses may be prepared as follows:

1-Methyl-3-carbamoyl-6-aminopyridinium iodide powder 50 gm is thoroughly mixed with 300 gm of gelatin powder USP. Each gelatin capsule size No. 0 filled with this mixture contains 50 mg of 1-methyl-3-carbamoyl-6-aminopyridinium iodide as an active ingredient.

Gelatin capsules containing 250 mg of 1-methyl-3-carbamoyl-6-aminopyridinium iodide in each capsule may also be prepared in the same way but without mixing with any gelatin powder.

EXAMPLE 10

1-Methyl-3-carbamoyl-6-aminopyridinium iodide for parenteral injections may be prepared as follows:

1-Methyl-3-carbamoyl-6-aminopyridinium iodide 0.3 g is dissolved in 10 ml saline and the solution in a sealed injection bottle is sterilized at 100° C. for 20 minutes. The parenteral composition thus prepared contains 3% of active ingredient, i.e. 30 mg per ml of 1-methyl-3-carbamoyl-6-aminopyridinium iodide.

EXAMPLE 11

1-Carbamoylmethyl-3-carbamoyl-6-aminopyridinium iodide for parenteral injections may be prepared as follows:

1-Carbamoylmethyl-3-carbamoyl-6-aminopyridinium iodide 0.1 g is dissolved in 10 ml saline, and the solution, sealed in an injection bottle, is sterilized at 100° C. for 20 minutes. The parenteral composition thus prepared contains 1% of active ingredient, i.e. 10 mg per ml of 1-carbamoylmethyl-3-carbamoyl-6-aminopyridinium iodide.

Animal Studies (1) Acute and Subacute Toxicity

One hundred twenty mice were administered subcutaneously with either 1-methyl-3-carbamoyl-6-aminopyridinium iodide or 1-carbamoylmethyl-3-carbamoyl-6-aminopyridinium iodide at various doses in single injections. It was found that 1-methyl-3-carbamoyl-6-aminopyridinium iodide at doses up to 400 mg/kg was nontoxic i.e. all mice were alive and healthy at the end of 5 weeks after the administration of the test substance. The LD$_{50}$ of 1-methyl-3-carbamoyl-6-aminopyridinium iodide was found to be higher than 800 mg/kg.

Under the same conditions it was found that 1-carbamoylmethyl-3-carbamoyl-6-aminopyridinium iodide at doses up to 1 g/kg was nontoxic.

(2) Chronic Toxicity

Thirty mice were administered subcutaneously 1-methyl-3-carbamoyl-6-aminopyridinium iodide in weekly doses of 50 mg/kg for six months. It was found that 1-methyl-3-carbamoyl-6-aminopyridinium iodide in a total dose of 1,250 mg/kg at a weekly dose of 50 mg/kg over six month periods was nontoxic for mice.

Four guinea pigs were administered subcutaneously 1-methyl-3-carbamoyl-6-aminopyridinium iodide in weekly doses of 50 mg/kg for six months.

It was found that 1-methyl-3-carbamoyl-6-aminopyridinium iodide in a total dose of 1,250 mg/kg at a weekly dose of 50 mg/kg over six month periods was nontoxic for guinea pigs.

Clinical Tests

(1) Psoriasis

A. Topical Administration

The involved skin in psoriasis is hyperplastic (thickened), erythematous (red or inflamed), and has thick adherent scales. The degree of thickening is such that lesions are elevated up to 1 mm above the surface of adjacent normal skin; erythema is usually an intense red; the thickened adherent scales cause the surface of involved skin to be markedly rough and uneven. These three attributes of thickness, color and texture can be quantified to allow objective measurement of degree of improvement from topically applied therapeutic test materials as follows:

|  | Degree of Improvement | | | | |
|---|---|---|---|---|---|
|  | None (0) | Mid (1+) | Moderate (2+) | Substantial (3+) | Complete (4+) |
| Thickness | Highly elevated | Detectable reduction | Readily apparent | Barely elevated | Normal thickness |
| Texture | Visibly rough | Palpably rough | Uneven but not rough | Slightly uneven | Visibly and palpably smooth |
| Color | Intense red | Red | Dark pink | Light pink | Normal skin color |

By means of such parameters degree of change in lesion can be numerically noted and comparisons made of one treated site to another.

In order to evaluate the compounds of this invention a total of 26 patients having psoriasis were tested with the composition as follows:

Therapeutic compositions containing 3-carbamoyl-6-aminopyridinium compounds of this invention prepared according to the foregoing Examples were topically administered to patients having psoriasis.

Test areas were kept to minimal size convenient for topical application, i.e. circles approximately 4 cm in diameter. The medicinal creams were topically applied by the patient in an amount (usually about 0.1 milliliter) sufficient to cover the test site. Applications were made three times daily and without occlusive dressings. Test periods did not exceed three weeks, and applications were discontinued at any time when resolution of the lesion on the test area was clinically judged to be complete.

TABLE 1

Effects on Psoriasis of Topical 3-Carbamoyl-6-aminopyridinium Compounds

| COMPOUNDS | Number of Patients | Therapeutic Effectiveness |
|---|---|---|
| 1-Methyl-3-carbamoyl-6-aminopyridinium iodide | 16 | 3+ |
| 1-Methyl-3-carbamoyl-6-aminopyridinium chloride | 9 | 3+ |
| 1-Methyl-3-carbamoyl-6-aminopyridinium hydroxide | 6 | 3+ |
| 1-Carbamoylmethyl-3-carbamoyl-6-aminopyridinium iodide | 12 | 4+ |

B. Intralesional Injection

Six patients with discrete plaque lesions of psoriasis participated in this study.

Injection solutions containing 1% 3-carbamoyl-6-aminopyridinium compounds were prepared according to the Examples. Duplicate lesions for each test material on the same patient were selected for intralesional administration. Each lesion, ranging in size from 2-to-5 cm in diameter, was carefully examined for its three attributes of thickness, color and texture. Intralesional injections of test solutions containing 1% 1-methyl-3-carbamoyl-6-aminopyridinium iodide or 1-carbamoylmethyl-3-carbamoyl-6-aminopyridinium iodide in an amount of 0.1 ml were administered. Parameters used in clinical evaluation of degree of improvement were the same as that described in the previous section (A).

The test results on psoriatic patients are summarized on the following table.

TABLE 2

Intralesional administration of 3-carbamoyl-6-aminopyridinium compounds on psoriasis

| COMPOUNDS | Number of Patients | Therapeutic Effectiveness |
|---|---|---|
| 1-Methyl-3-carbamoyl-6-aminopyridinium iodide | 5 | 2+ |
| 1-Carbamoylmethyl-3-carbamoyl-6-aminopyridinium iodide | 6 | 4+ |

C. Oral Administration

Three patients having generalized psoriasis participated in this study. Oral preparations containing 1-methyl-3-carbamoyl-6-aminopyridinium iodide in gelatin capsules at a dosage of 50 mg or 250 mg per each capsule were formulated according to the Example. The patients were instructed to take orally one capsule to three capsules daily for two weeks. Parameters used in clinical evaluation of degree of improvement were the same as that described in the previous section (A).

Two patients showed substantial improvement of psoriatic lesions after two weeks of oral administration of 1-methyl-3-carbamoyl-6-aminopyridinium iodide at a *daily* dosage of 2 mg/kg. The remaining one patient showed moderate improvement of psoriatic lesions after two weeks of oral administration of 1-methyl-3-carbamoyl-6-aminopyridinium iodide at a daily dosage of 3 mg/kg.

(2) Dry Skin

The involved skin in severe dry skin is hyperplastic (thickened) and has thick adherent scales. The degree of thickening is such that lesions are palpably and visually elevated. The thickened adherent scales cause the surface of involved skin to be markedly rough and uneven. These two attributes of thickness and texture can be quantified to allow objective measurement of degree of improvement from topically applied therapeutic test materials as follows:

|  | None (0) | Mid (1+) | Moderate (2+) | Substantial (3+) | Complete (4+) |
|---|---|---|---|---|---|
| Thickness | Distinctly thickened | Detectable reduction | Readily apparent reduction | Barely thickened | Normal thickness |
| Texture | Visibly rough | Palpably rough | Uneven but not rough | Slightly uneven | Visibly and palpably smooth |

By means of such parameters degrees of change in lesion can be numerically noted and comparisons made of one treated site to another.

In order to evaluate the 3-carbamoyl-6-aminopyridinium compounds of this invention four patients with severe dry skin conditions of ichthyosis were treated with the compositions as described in the Examples.

Treated areas were of a size convenient for topical applications, i.e. circles 4 cm in diameter demarcated with a plastic ring of that size inked on a stamp pad. The medicinal cream or ointments were topically applied by the patient in an amount (usually about 0.1 cubic milliliter) sufficient to cover the treatment site. Applications were made three times daily and without occlusive dressings. Application periods did not exceed three weeks, and applications were discontinued at any time when resolution of the lesion on the treatment area was clinically judged to be complete. Clinical evaluations of degree of improvement were made at intervals of daily to weekly.

The test results on patients with severe dry skin are summarized on the following table.

TABLE 3

Topical Effectiveness of 3-Carbamoyl-6-aminopyridinium Compounds on Severe Dry Skin

| COMPOUNDS | Number of Patients | Therapeutic Effectiveness |
|---|---|---|
| 1-Methyl-3-carbamoyl-6-aminopyridinium iodide | 3 | 2+ |
| 1-Carbamoylmethyl-3-carbamoyl-6-aminopyridinium iodide | 4 | 4+ |

(3) Darier's Disease

Two patients with Darier's disease were instructed to apply topically three times daily to the circumscribed lesions the therapeutic compositions containing 3-carbamoyl-6-aminopyridinium compounds prepared according to the Examples.

Parameters used in measuring degree of improvement from topically applied therapeutic compositions were the same as that described in the previous section of severe dry skin with slight modifications.

The test results on patients with Darier's disease are summarized on the following table.

TABLE 4

Topical Effectiveness of 3-Carbamoyl-6-aminopyridinium Compounds on Darier's Disease

| COMPOUNDS | Number of Patients | Therapeutic Effectiveness |
|---|---|---|
| 1-Methyl-3-carbamoyl-6-aminopyridinium iodide | 2 | 2+ |
| 1-Carbamoylmethyl-3-carbamoyl-6-aminopyridinium iodide | 2 | 3+ |

(4) Pityriasis rubra pilaris

Two patients with pityriasis rubra pilaris were instructed to apply topically three times daily to the circumscribed lesions the therapeutic compositions containing 3-carbamoyl-6-aminopyridinium compounds prepared according to the Examples.

Parameters used in measuring degree of improvement from topically applied therapeutic compositions were the same as that described in the previous section of psoriasis with slight modifications.

The test results on patients with pityriasis rubra pilaris are summarized on the following table.

TABLE 5

Topical Effectiveness of 3-Carbamoyl-6-aminopyridinium Compounds on Pityriasis Rubra Pilaris

| COMPOUNDS | Number of Patients | Therapeutic Effectiveness |
|---|---|---|
| 1-Methyl-3-carbamoyl-6-aminopyridinium iodide | 2 | 2+ |
| 1-Carbamoylmethyl-3-carbamoyl-6-aminopyridinium iodide | 2 | 3+ |

(5) Sèzary's Syndrome

Three patients having Sèzary's syndrome participated in this study. The patients were instructed to apply topically three times daily to the circumscribed lesions the therapeutic compositions containing 3-carbamoyl-6-aminopyridinium compounds prepared according to the Examples.

Parameters used in measuring degree of improvement from topically applied therapeutic compositions were the same as that described in the previous section of psoriasis with slight modifications.

The test results on patients with Sèzary's syndrome are summarized on the following table.

TABLE 6
Topical Effectiveness of 3-Carbamoyl-6-aminopyridinium Compounds on Sezary's Syndrome

| COMPOUNDS | Number of Patients | Therapeutic Effectiveness |
|---|---|---|
| 1-Methyl-3-carbamoyl-6-aminopyridinium iodide | 3 | 2+ |
| 1-Carbamoylmethyl-3-carbamoyl-6-aminopyridinium iodide | 3 | 3+ |

In summary, this invention includes the discovery of methods and compositions containing 3-carbamoyl-6-aminopyridinium compounds which are therapeutically useful for alleviating the symptoms of various skin disorders and specifically including inflammatory skin disorders and disorders of keratinization. The skin disorders may include psoriasis, eczema, dermatitis, Darier's disease, pityriasis rubra pilaris, Sèzary's syndrome, dry skin, ichthyosis, keratoses, lichen simplex chronicus, acne, pruritus and warts. The administration includes topical application, oral administration and parenteral injections.

The invention may be embodied in other specific forms without departing from the spirit or essential characteristics thereof. The present embodiment is, therefore, to be considered in all respects as illustrative and not restrictive, the scope of the invention being indicated by the appended claims and all changes which come within the meaning and range of equivalency of the claims are, therefore, intended to be embraced therein.

What is claimed is:

1. A 6-aminonicotinamide pyridinium compound effective on topical or systemic administration to alleviate the symptoms of skin disorders due to inflammation and disturbed keratinization comprising:
   a compound having the formula:

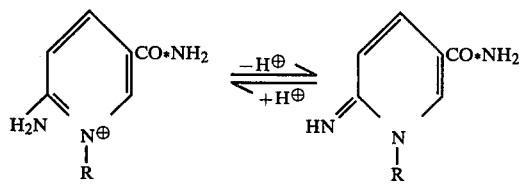

wherein:
   $O* = O$ or $S$
   $R =$ a lower alkyl, carbamoyl lower alkyl, phenyl, phenyl lower alkyl or carboxy lower alkyl group
   or its intermolecular salt with a therapeutically or pharmaceutically acceptable organic or inorganic acid anion, or its intramolecular salt with a carboxylic acid anion.

2. A 6-aminonicotinic acid pyridinium compound effective on topical or systemic administration to alleviate the symptoms of skin disorders due to inflammation and disturbed keratinization comprising:
   a compound having the formula:

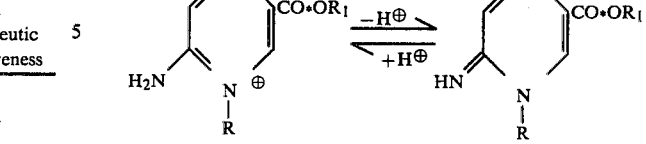

wherein:
   $O* = O$ or $S$
   $R =$ a lower alkyl, carbamoyl lower alkyl, phenyl, phenyl lower alkyl, or carboxy lower alkyl group
   $R_1 =$ H or an organic or inorganic cation or its intermolecular salt with a therapeutically or pharmaceutically acceptable organic or inorganic anion, or its intramolecular salt with a carboxylic acid anion.

3. A 6-aminonicotinate pyridinium compound effective on topical or systemic administration to alleviate the symptoms of skin disorders due to inflammation and disturbed keratinization comprising:
   a compound having the formula:

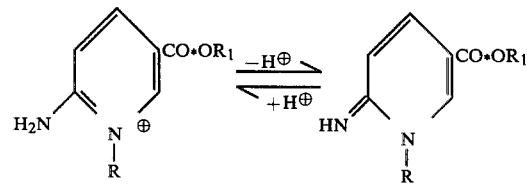

wherein:
   $O* = O$ or $S$
   $R =$ a lower alkyl, carbamoyl lower alkyl, phenyl, phenyl lower alkyl or carboxy lower alkyl group
   $R_1 =$ an alkyl radical having from 1-to-9 carbon atoms or an aryl radical having from 6 to 9 carbon atoms
   or its intermolecular salt with a therapeutically or pharmaceutically acceptable organic or inorganic anion or its intramolecular salt with a carboxylic acid anion.

4. A therapeutic composition for alleviating the symptoms of skin disorders due to inflammation and disturbed keratinization comprising the compound of claim 1 present in an anti-inflammatory therapeutically effective amount in a pharmaceutically acceptable vehicle for topical administration.

5. The composition of claim 4 wherein said compound is present in from about 0.01 to 5 percent by weight of the total composition.

6. A systemic dosage for alleviating the symptoms of skin disorders in humans due to inflammation and disturbed keratinization comprising: an orally administrable, antiflammatory therapeutically effective amount of the compound of claim 1 in pharmaceutically acceptable capsules or tablets for oral administration.

7. The dosage of claim 6 wherein said capsules or tablets contain from about 1 to 50 mg/kg of body weight of the human to be treated.

8. A systemic composition for parenteral injection for alleviating the symptoms of skin disorders in humans due to inflammation and disturbed keratinization comprising: an anti-inflammatory therapeutically effective amount of the compound of claim 1 in a pharmaceutically acceptable liquid solvent or suspension agent for parenteral injection.

9. The composition of claim 8 wherein said compound is present in saline solution in a concentration of from about 1 to 5 percent by weight.

10. A therapeutic composition for alleviating the symptoms of skin disorders due to inflammation and disturbed keratinization comprising the compound of claim 2 present in an anti-inflammatory therapeutically effective amount in a pharmaceutically acceptable vehicle for topical administration.

11. The composition of claim 10 wherein said compound is present in from about 0.01 to 5 percent by weight of the total composition.

12. A systemic dosage for alleviating the symptoms of skin disorders in humans due to inflammation and disturbed keratinization comprising: an orally administrable, anti-inflammatory therapeutically effective amount of the compound of claim 2 in pharmaceutically acceptable capsules or tablets for oral administration.

13. The dosage of claim 12 wherein said capsules or tablets contain from about 1 to 50 mg/kg of body weight of the human to be treated.

14. A systemic composition for parenteral injection for alleviating the symptoms of skin disorders in humans due to inflammation and disturbed keratinization comprising: an antiinflammatory therapeutically effective amount of the compound of claim 2 in a pharmaceutically acceptable liquid solvent or suspension agent for parenteral injection.

15. The composition of claim 14 wherein said compound is present in saline solution in a concentration of from about 1 to 5 percent by weight.

16. A therapeutic composition for alleviating the symptoms of skin disorders due to inflammation and disturbed kertinization comprising the compound of claim 3 present in an antiinflammatory therapeutically effective amount in a pharmaceutically acceptable vehicle for topical administration.

17. The composition of claim 16 wherein said compound is present in from about 0.01 to 5 percent by weight of the total composition.

18. A systemic dosage for alleviating the symptoms of skin disorders in humans due to inflammation and disturbed keratinization comprising: an orally administrable, antiinflammatory therapeutically effective amount of the compound of claim 3 in pharmaceutically acceptable capsules or tablets for oral administration.

19. The dosage of claim 18 wherein said capsules or tablets contain from about 1 to 50 mg/kg of body weight of the human to be treated.

20. A systemic composition for parenteral injection for alleviating the symptoms of skin disorders in humans due to inflammation and disturbed keratinization comprising: an antiinflammatory therapeutically effective amount of the compound of claim 3 in a pharmaceutically acceptable liquid solvent or suspension agent for parenteral injection.

21. The treatment of claim 20 wherein said compound is present in saline solution in a concentration of from about 1 to 5 percent by weight.

22. A method for treating the symptoms of skin disorders in humans due to inflammation and disturbed keratinization comprising: topically administering to involved skin a symptom alleviating effective amount of a compound having the formula:

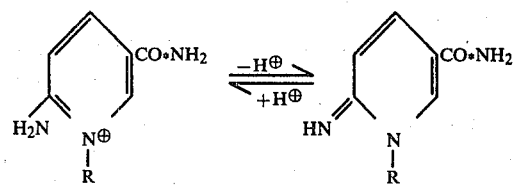

wherein:
O*=O or S
R=a lower alkyl, carbamoyl lower alkyl, phenyl, phenyl lower alkyl, or carboxy lower alkyl group or its intermolecular salt with a therapeutically or pharmaceutically acceptable organic or inorganic anion, or its intramolecular salt with a carboxylic acid anion, in a pharmaceutically acceptable vehicle for topical administration.

23. A method for treating the symptoms of skin disorders in humans due to inflammation and disturbed keratinization comprising: topically administering to involved skin a symptom alleviating effective amount of a compound having the formula:

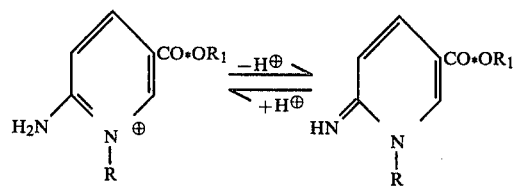

wherein:
O*=O or S
R=a lower alkyl, carbamoyl lower alkyl, phenyl, phenyl lower alkyl or carboxy lower alkyl group
$R_1$=H or an organic or inorganic cation or its intermolecular salt with a therapeutically or pharmaceutically acceptable organic or inorganic anion, or its intramolecular salt with a carboxylic anion, in a pharmaceutically acceptable vehicle for topical administration.

24. A method for treating the symptoms of skin disorders in humans due to inflammation and disturbed keratinization comprising: topically administering to involved skin a symptom alleviating effective amount of a compound having the formula:

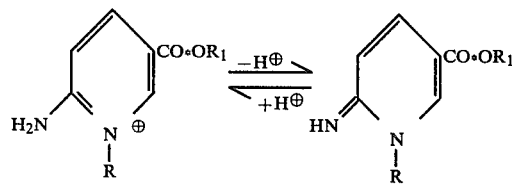

wherein:
O*=O or S
R=a lower alkyl, carbamoyl lower alkyl, phenyl, phenyl lower alkyl or carboxy lower alkyl group
$R_1$=an alkyl radical having from 1-to-9 carbon atoms or an aryl radical having from 6-to-9 carbon atoms or its intermolecular salt with a therapeutically or pharmaceutically acceptable organic or inorganic anion or its intramolecular salt with a carboxylic acid anion, in a 25. The method of claim 22 wherein said compound is present in a concentration of from about 0.01 to 5 percent by weight.

26. The method of claim 23 wherein said compound is present in a concentration of from about 0.01 to 5 percent by weight.

27. The method of claim 24 wherein said compound is present in a concentration of from about 0.01 to 5 percent by weight.

28. A method for treating the symptoms of skin disorders in humans due to inflammation and disturbed keratinization comprising: administering a therapeutic and symptom alleviating effective amount in total dosage of from 1 to 50 mg/kg body weight of a compound having the formula:

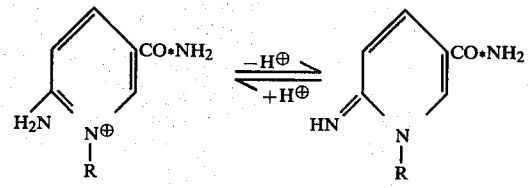

wherein:

O*=O or S

R=a lower alkyl, carbamoyl lower alkyl, phenyl, phenyl lower alkyl, or carboxy lower alkyl group or its intermolecular salt with a therapeutically or pharmaceutically acceptable organic or inorganic anion, or its intramolecular salt with a carboxylic acid anion.

29. A method for treating the symptoms of skin disorders in humans due to inflammation and disturbed keratinization comprising: administering a therapeutic and symptom alleviating effective amount in total dosage of from 1 to 50 mg/kg of body weight of a compound having the formula:

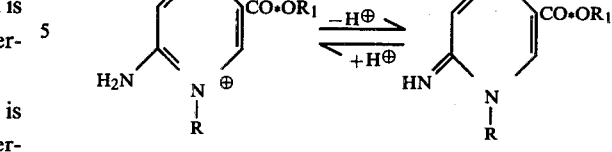

wherein:

O*=O or S

R=a lower alkyl, carbamoyl lower alkyl, phenyl, phenyl lower alkyl or carboxy lower alkyl group $R_1$=H or an organic or inorganic cation or its intermolecular salt with a therapeutically or pharmaceutically acceptable organic or inorganic anion, or its intramolecular salt with a carboxylic acid anion.

30. A method for treating the symptoms of skin disorders in humans due to inflammation and disturbed keratinization comprising: administering a therapeutic and symptom alleviating effective amount in total dosage of 1 to 50 mg/kg body weight of a compound having the formula:

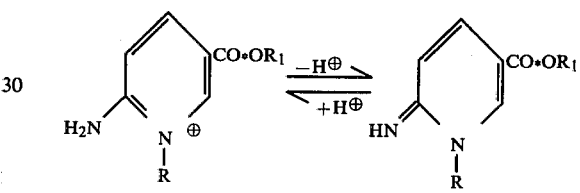

wherein:

O*=O or S

R=a lower alkyl, carbamoyl lower alkyl, phenyl, phenyl lower alkyl or carboxy lower alkyl group $R_1$=an alkyl radical having from 1-to-9 carbon atoms or an aryl radical having from 6-to-9 carbon atoms or its intermolecular salt with a therapeutically or pharmaceutically acceptable organic or inorganic anion or its intramolecular salt with a carboxylic acid anion.

31. The method of claim 28 wherein said compound is administered orally.

32. The method of claim 29 wherein said compound is administered orally.

33. The method of claim 30 wherein said compound is administered orally.

* * * * *